(12) United States Patent
Hartman et al.

(10) Patent No.: US 7,637,729 B2
(45) Date of Patent: Dec. 29, 2009

(54) MODULAR ARTICULATING CEMENT SPACER MOLD

(75) Inventors: William Hartman, Warsaw, IN (US); H. Gene Hawkins, Warsaw, IN (US); Kristen Martin, Wakarusa, IN (US); Jacob Wilson, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 69 days.

(21) Appl. No.: 11/955,601

(22) Filed: Dec. 13, 2007

(65) Prior Publication Data

US 2009/0157189 A1 Jun. 18, 2009

(51) Int. Cl.
*A61F 2/36* (2006.01)

(52) U.S. Cl. .......................... 425/116; 249/55; 249/61; 249/97; 249/102

(58) Field of Classification Search ............... 249/55, 249/61, 95, 97, 102; 425/2, 116; 623/901
See application file for complete search history.

(56) References Cited

U.S. PATENT DOCUMENTS

| | | | |
|---|---|---|---|
| 3,102,536 A | 9/1963 | Rose et al. | |
| 4,721,390 A | 1/1988 | Lidgren et al. | |
| 4,950,300 A * | 8/1990 | Langlais | 623/22.44 |
| 4,957,510 A * | 9/1990 | Cremascoli | 623/22.46 |
| 5,108,452 A | 4/1992 | DeMane et al. | |
| 5,133,771 A * | 7/1992 | Duncan et al. | 623/23.2 |
| 5,328,262 A | 7/1994 | Lidgren et al. | |
| 5,370,221 A | 12/1994 | Magnusson et al. | |
| 5,443,523 A * | 8/1995 | Mikhail | 623/23.37 |
| 5,501,520 A | 3/1996 | Lidgren et al. | |
| 5,858,020 A | 1/1999 | Johnson et al. | |
| 5,951,160 A | 9/1999 | Ronk | |
| 6,155,812 A | 12/2000 | Smith et al. | |
| 6,221,110 B1 * | 4/2001 | Copf | 623/22.21 |
| 6,286,670 B1 | 9/2001 | Smith | |
| 6,361,731 B1 | 3/2002 | Smith et al. | |
| 2003/0065398 A1 | 4/2003 | Cueille et al. | |
| 2005/0004680 A1 | 1/2005 | Saladino et al. | |

(Continued)

FOREIGN PATENT DOCUMENTS

EP 166724 1/1986

(Continued)

OTHER PUBLICATIONS

Schoellner et al, Individual Bone Cement Spacers (IBCS) for Septic Hip Revision-Preliminary Report, May 2003, Arch Orthop Trauma Surg, Springer-Verlag, pp. 254-259.*

(Continued)

*Primary Examiner*—Robert B Davis
(74) *Attorney, Agent, or Firm*—Harness, Dickey

(57) ABSTRACT

The present teachings provide a modular articulating cement spacer mold for forming a temporary implant. The modular spacer mold includes a head component mold defining a first opening, a head connector positioned within the first opening of the head component mold, a stem component mold defining a second opening, and a stem connector to fit within the second opening of the stem component mold to mateably engage the head connector. Related kits and methods of forming a temporary implant are provided.

25 Claims, 6 Drawing Sheets

U.S. PATENT DOCUMENTS

| | | | |
|---|---|---|---|
| 2005/0027302 | A1 | 2/2005 | Cueille et al. |
| 2005/0143828 | A1 | 6/2005 | Collins et al. |
| 2006/0109737 | A1 | 5/2006 | Wilander |
| 2007/0016215 | A1 | 1/2007 | Wilander et al. |
| 2007/0222114 | A1 | 9/2007 | Ziran et al. |
| 2008/0058950 | A1* | 3/2008 | Leonard et al. ............ 623/22.4 |
| 2009/0146342 | A1* | 6/2009 | Haney et al. ................ 264/250 |

FOREIGN PATENT DOCUMENTS

| | | |
|---|---|---|
| FR | 2898039 | 9/2007 |
| WO | WO-9851240 | 11/1998 |

OTHER PUBLICATIONS

Biomet Orthopedics, Inc., "The Optivac® Vacuum Mixing System, Intelligent Simplicity," brochure, 2000 (12 pages).

Biomet, "Mixing and Delivery: Optivac®", pp. 1-2, available at http://www.bonecement.com/index.php?id=16933, printed Jul. 15, 2008.

Biomet, "Optivac® Procedure Set," pp. 1-2, available at http://www.bonecement.com/index.php?id=17149, last visited Jul. 15, 2008.

Biomet, Inc., "Optivac® Fusion™ Vacuum Mixing Bowl," pp. 1-2, 2001-2008, available at http://www.biomet.com/hcp/prodpage.cfm?c=0F&p=090505 (printed Feb. 4, 2008).

Biomet, Inc., "Optivac® Vacuum Mixing System," 2001-2008, pp. 1-2, available at http://www.biomet.com/hcp/prodpage.cfm?c=0F&p=0A0403 (printed Feb. 4, 2008).

DePuy Orthopaedics, Inc., "Prostalac Hip Temporary Prosthesis", pp. 1-2, 2001, available at http:/www.fda.gov/cdrh/mda/docs/h000004.html, printed Feb. 8, 2007 (2 pages).

DePuy, "Prostalac® Hip", pp. 1-2, 2005-2006, available at http://www.jnjgateway.com/home.jhtml?page=viewContent&contentId=09008b98800540d1&loc=USENG, printed Feb. 8, 2007 (2 pages).

Exactech, Inc., "InterSpace® Hip," p. 1, available at http://www.exac.com/products/cement-spacers/interspace-hip, last visited Jul. 15, 2008.

Johnson & Johnson, "Prostalac® Hip Essential Product Information," p. 1-3, available at http://www.jnjgateway.com/home.jhtml?contentID=09008b9880054123&loc=USENG&page=viewContent, last visited Jul. 15, 2008.

International Search Report and Written Opinion for PCT/US2008/085529 mailed Mar. 17, 2009 claiming priority to U.S. Appl. No. 11/955,601, filed Dec. 13, 2007.

* cited by examiner

MODULAR ARTICULATING CEMENT SPACER MOLD

FIELD

The present disclosure relates to a hip spacer mold, and more particularly, to a modular articulating two-stage cement hip spacer mold.

BACKGROUND

A natural joint may undergo degenerative changes due to a variety of etiologies. When these degenerative changes become so far advanced and irreversible, it may ultimately become necessary to replace the natural joint with a joint prosthesis. However, due to any number of reasons, a small portion of patients that undergo such orthopedic surgical procedures suffer from infections at the surgical site and generally around the implanted joint prosthesis. In order to cure such an infection in a two-stage re-implantation, the implanted joint prosthesis is generally removed, the site is thoroughly debrided and washed, antibiotics are applied to the infected site via a temporary implant until the infection is eliminated, and a new revision type joint prosthesis is then implanted during a subsequent orthopedic surgical procedure.

Accordingly, there is a need for apparatus and methods to facilitate two-stage re-implantation which expedite healing at the site, provide a better fitting implant, reduce the amount of time a patient is bedridden, increase the efficiency of the surgical procedure while reducing the surgical time and cost, eliminate any re-cleaning or re-sterilizing steps, and create a customizable procedure.

SUMMARY

In various embodiments, the present teachings relate to a modular articulating cement spacer mold for forming a temporary implant. The modular spacer mold includes a head component mold defining a first opening, a head connector positioned within the first opening of the head component mold, a stem component mold defining a second opening, and a stem connector to fit within the second opening of the stem component mold to mateably engage the head connector.

In other embodiments, the present teachings provide kits for forming modular articulating cement spacer molds for temporary implants. The kits include at least one head component mold and at least one stem component mold.

The present teachings further provide methods for forming a temporary implant. A bone cement is mixed during a surgical procedure. The appropriately sized head component mold, head component connector, stem component mold, and stem connector are selected. The head component mold and the stem component mold are filled with the cement to form the temporary implant which is implanted into the patient.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Although certain examples and surgical methods disclosed herein are in conjunction with a temporary hip implant, it is understood that the molds and surgical methods disclosed herein can be used in any orthopedic revision surgery for any area in the patient.

Figure 1:
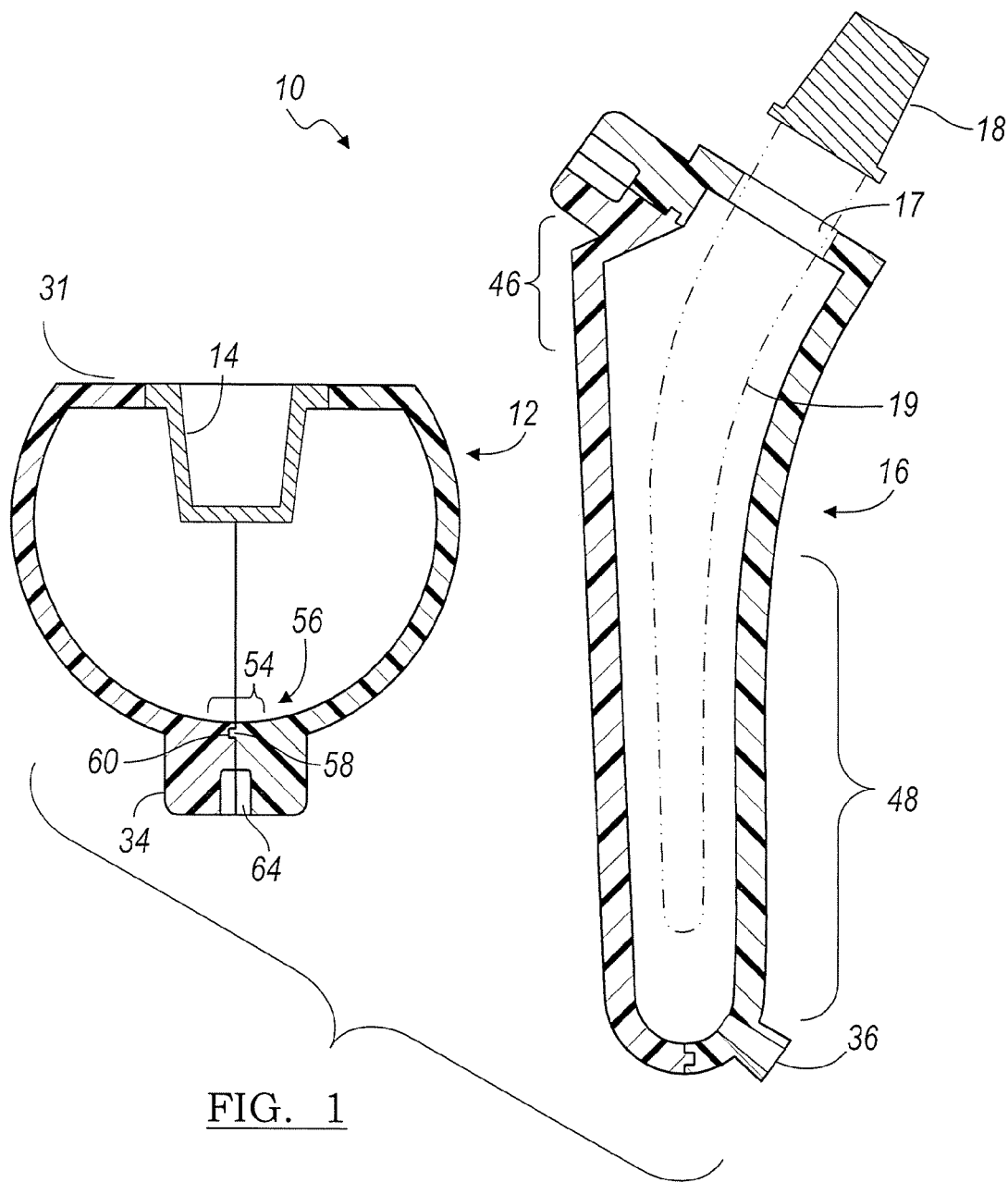
FIG. 1 depicts a modular cement mold according to various embodiments.

FIG. 1 depicts a modular cement mold 10 according to the present teachings. The modular cement mold 10 is used to form a temporary femoral hip implant or prosthesis to replace a right of left portion of a femoral hip joint for a temporary healing period. The modular cement mold 10 can be formed from any biocompatible material including various polymers. In various embodiments, the polymeric material can be readily tearable and/or translucent, such as a thermoplastic elastomer. In various embodiments, the thermoplastic elastomer is silicone. In such embodiments, the silicone selected can have a sufficiently high stiffness such that the modular cement mold 10 will not sag or be deformed upon handling. An exemplary silicone that achieves these characteristics is Dow Q7-4780 or any other 80 durometer silicone. Moreover, it should be noted that the material selected should generally not adversely react with the bone cement and antibiotic selected. The modular cement mold 10 can also be made of any other appropriate materials, including, but not limited to rubber.

The modular cement mold 10 includes a head component mold 12 having a head connector 14 therein and a stem component mold 16 having an opening 17 for a stem connector 18. It is understood that various features from the head component mold 12 and the stem component mold 16 can be interchanged within the scope of the present teachings. The modularity of the present teachings allows the surgeon to create a highly customized implant based on both the head and the stem size needs of the patient. This is beneficial in revision surgery where the condition of either the acetabulum or the femur may differ to the extent where a monolithic temporary implant may not best meet the needs of the patient. By providing the head connector and the stem connector, and/or the various reinforcements as detailed later herein, embodiments of the present temporary implant are optimized for strength and reinforce the high stress areas along the neck of the implant.

Figure 3:
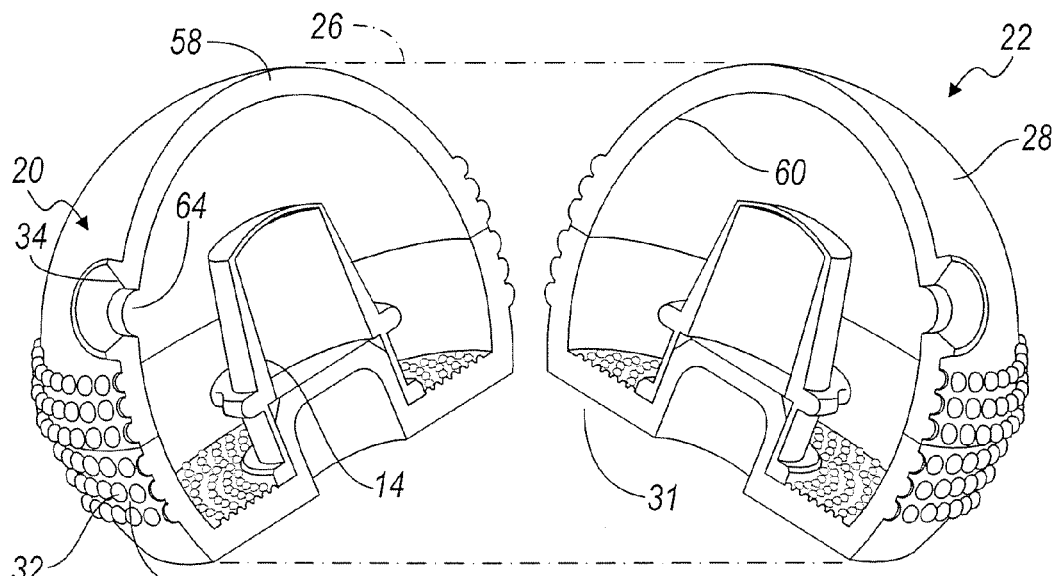
FIG. 3 depicts an exploded view of the head component mold.

As shown in FIG. 3, the femoral head component mold 12 includes a first half 20 and a second half 22 which provide the articulating head of the temporary implant. The femoral head component first half 20 and second half 22 can be joined along center line 26 which corresponds to the coronal plane of the subsequently formed temporary hip implant. The halves 20 and 22 are essentially mirror images of one another and like reference numerals will be used to identify like structures for each half.

Figure 10:
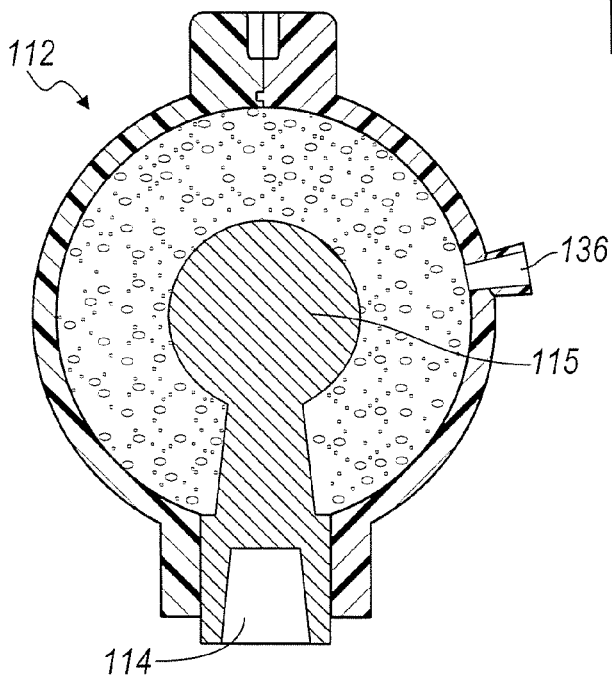
FIG. 10 depicts a head component having a stepped and tapered reinforcing head connector therein.
Figure 11:
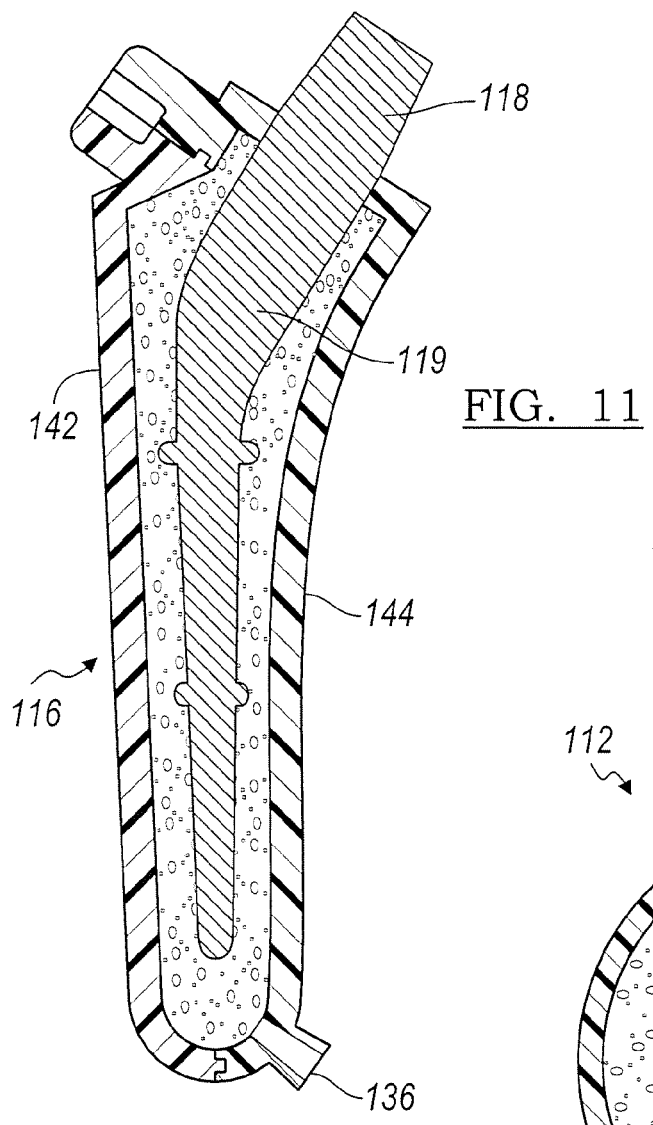
FIG. 11 depicts a stem component having a reinforcing stem connector therein.
Figure 12:
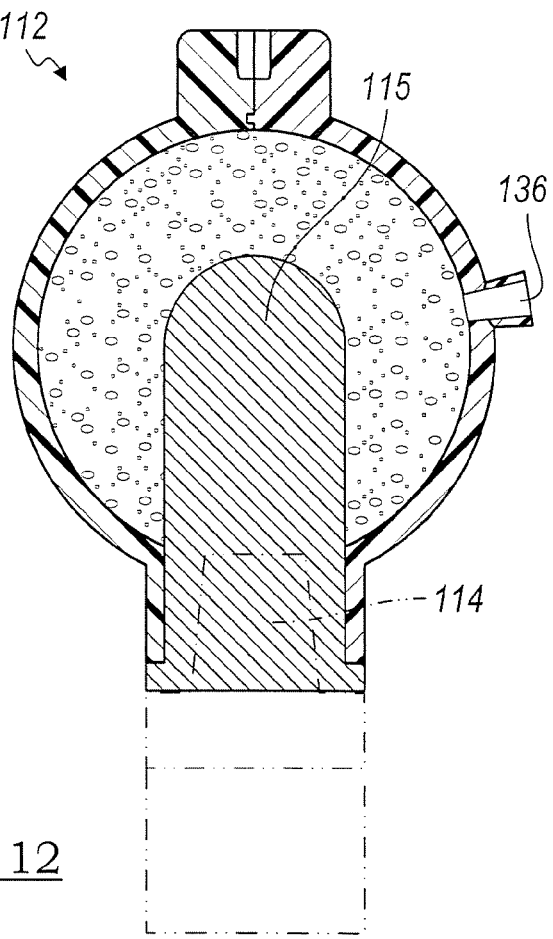
FIG. 12 depicts a head component having a reinforcing head connector therein.

The halves 20 and 22 include an outer hemispherical sidewall 28 and an inner hemispherical sidewall 30 which define the entire shape of the substantially spherical articulating head. The substantially spherical articulating head and thus, the mold halves 20 and 22 can include a flattened region 31 as shown in FIGS. 1 and 3. The flattened region 31 can be placed opposite the articulating portion of the head so as to not hinder articulation of the final implant. A variation of the substantially spherical head is also shown in FIGS. 8, 10, and 12. The inner hemispherical sidewall 30 can include surface area increasing features 32. Upon filling the head component mold 12, recess portions or depressions are left in the articulating head of the final implant which are the negative impression of the surface area increasing features 32. The depressions increase the surface area of the resultant articulating head. Suitable depressions include, but are not limited to grooves, dimples, hemispheres, cones, stars, ridges, notches, and the like. The depressions can also include individual letters or combinations of letters and designs, such as a logo. Certain shapes, such as multi-point stars or deep cones, provide the greatest increase in surface area. As shown in FIG. 3, the surface area increasing feature 32 can include rounded projections to define dimples in the temporary implant. Further, referring to FIG. 7, a variety of different surface area increasing features 32 are shown.

The same surface feature 32 can be included on each of the inner hemispherical side walls 30 or the surface features can be varied in size and/or shape within the same hemispherical side wall 30 or on both hemispherical sidewalls 30. The surface area of the temporary implant can be increased by from about 1% up to 50% or more depending on the combination of surface area increasing features 32. An exemplary, but non-limiting, benefit of the increased surface area is the increased amount of antibiotic or other therapeutic material (i.e.: drugs, vitamins, etc.) from the surface of the temporary implant to the defect site. The increased delivery of the antibiotic or other therapeutic material expedites healing and minimizes the recovery time of the patient. The head component mold 12 further includes a trapezoidal shaped foot 34 by which to grasp the head component mold 12.

The head connector 14 is used to connect the articulating head component of the finished product with the femoral stem component of the finished product. The head connector 14 can define a hollow cylindrical or tapered chamber formed by a metal insert contained within the head component mold 12. Exemplary metals for the head connector 14 include stainless steel, titanium, cobalt, and the like and various alloys thereof. The head connector 14 can mate with the femoral stem component using a taper fit, such as a Morse taper, as a non-limiting example. The head connector 14 can also include surface roughening features or a surface texture to facilitate placement and fit of the stem connector 18 with the head connector 14.

In various embodiments, the head connector 14 is a female connector and is contained within the head component mold 12 such that upon filling the head component mold 12 with a material, such as a bone cement, a void volume will be defined in the articulating head portion of the temporary implant having a volume that is roughly equivalent to the void volume defined by the head connector 14. In still other embodiments, the head connector 14 can be a male connector and is contained at a region of the head component and does not define a hollow region within the head component mold 12 upon filling the head mold with the material. In either embodiment, the head connector 14 is fixed in the head component mold 12 so that it is not inadvertently displaced.

The head connector 14 is retained in the head component mold 12 by a lip or ring about the lower region of the head connector 14 which has at least one dimension greater than the opening for the head connector 14. Any other suitable retention technique can also be employed in accords with the present teachings. For example, the head connector 14 can be retained in groove defined by the head component mold 12. Moreover, inclusion of the head connector 14 in the head component mold 12 maintains a material-tight integrity of the head component mold 12 and prevents leakage of a filling material therefrom. In various embodiments, the head component mold 12 and the head connector 14 are provided as a single unit where the head connector 14 is embedded in the material of the head component mold 12, as shown in FIG. 3.

Figure 6:
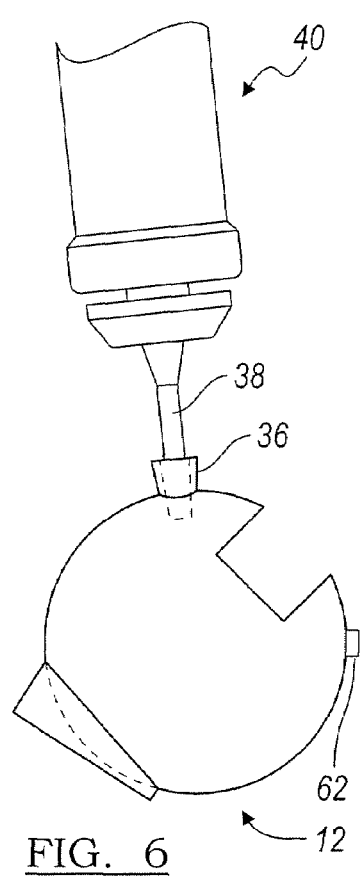
FIG. 6 depicts injection of a material into the head component mold according to various embodiments.

As best shown in FIG. 6, the head component mold 12 can further include an access port 36 through which to deliver a material to fill the head component mold 12. In various embodiments, the access port 36 can be defined at any region of the head component mold 12. The head access port 36 is implemented into the head component mold 12 as to maintain the material-tight integrity of the head component mold 12 and does not facilitate inadvertent removal of material from within the head component mold 12. As detailed later herein, the head access port 36 is mated with a nozzle 38 of a delivery device 40 through which a material is delivered to the head component mold 12.

Figure 4:
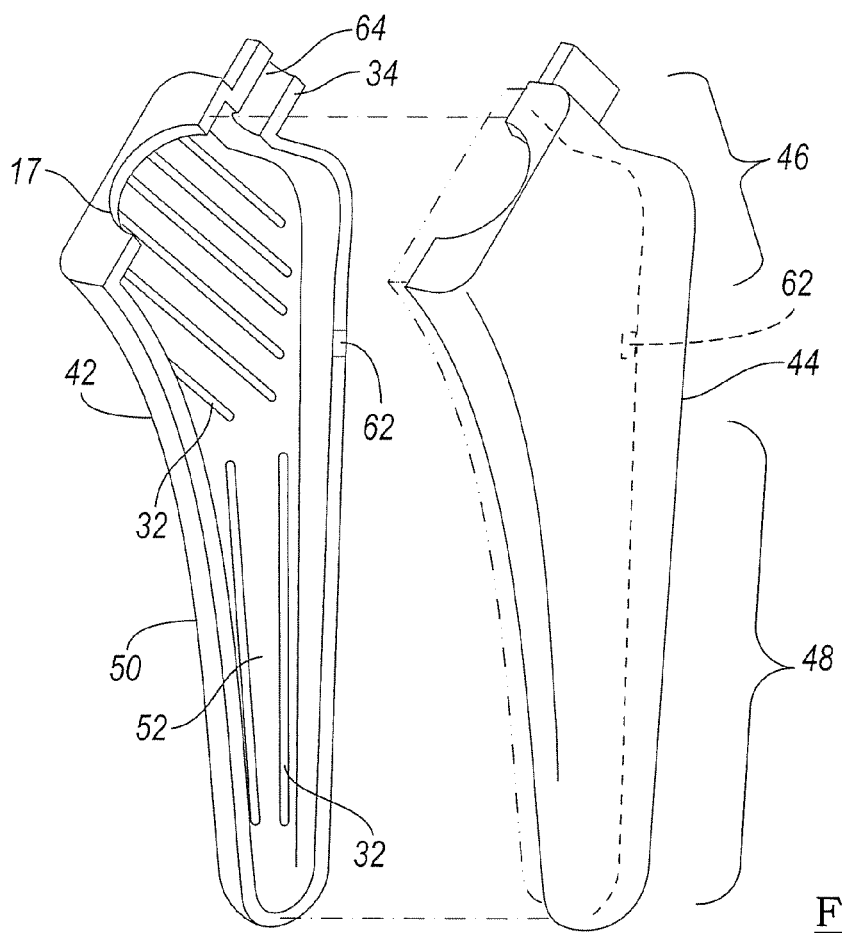
FIG. 4 depicts an exploded view of the stem component mold.
Figure 5:
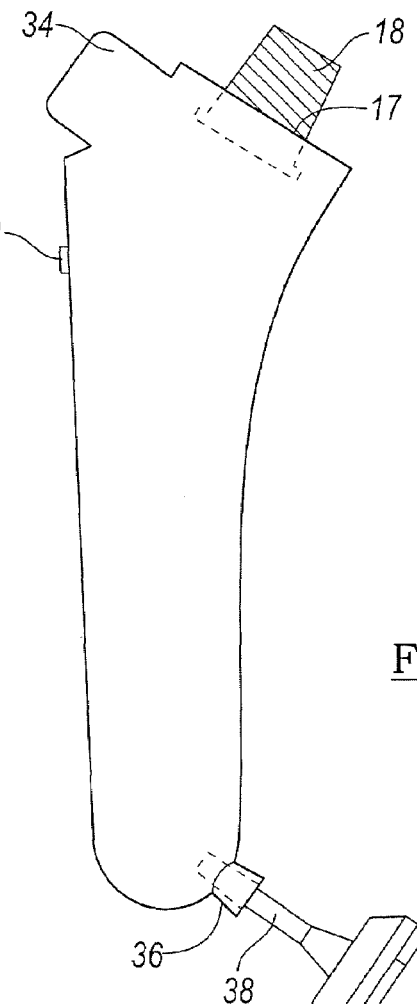
FIG. 5 depicts injection of a material into the stem component mold according to various embodiments.

Turning to FIGS. 4 and 5, the femoral stem component mold 16 includes a first half 42 and a second half 44. The halves 42 and 44 include an enlarged neck portion 46 and an elongated stem portion 48. As stated above herein, the halves 42 and 44 are essentially mirror images of one another, respectively, and like reference numerals will be used to identify like structures for each half. The neck portion 46 is enlarged to provide additional strength for the temporary implant.

The stem component mold 16 includes outer sidewalls 50 and inner sidewalls 52. As detailed above with respect to the head component mold 12, the stem component mold 16 can also include surface features 32 on the sidewalls 50 and 52. The surface area increasing features 32 can be continuous throughout the length of the stem component mold 16 or the surface area increasing features 32 can be varied in direction, size, or shape long the length of the stem component mold 16, such as the varied direction surface area increasing features 32 comprising grooves depicted in FIG. 4. In still other embodiments, the surface area increasing features 32 can be placed at only discrete regions along the stem component mold 16. It is understood that the surface area increasing features 32 on the stem component mold 16 can either match or be different from the surface area increasing features 32 on the head component mold 12.

Figure 2:
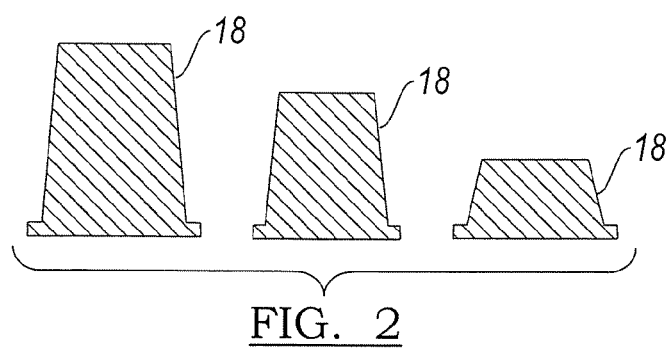
FIG. 2 depicts a series of neck adapters according to various embodiments.

Referring to FIGS. 1 and 2, the stem connector 18 is adapted to fit into the opening 17 as defined by the stem component mold 16. The stem connector 18 can have a slight taper, such as a Morse taper, as to provide the quick and tight fit with the head connector 14. The stem connector 18 can be made of any of the biocompatible metal materials detailed above herein for use with the head connector 14. As shown by the phantom lines, the stem connector 18 can also include a reinforcing rod 19 to extend the length of the stem component mold 16. Further description of the reinforcing feature is provided later herein.

The stem connector 18 can also include surface roughening features or a surface texture to facilitate placement and fit of the stem connector 18 with the head connector 14. As shown in FIG. 2, the stem connector 18 can be made in differing lengths and widths to provide further customization of the temporary implant depending on the patient's needs.

The halves 20 and 22 of the head component mold 12 and the halves 42 and 44 of the stem component mold 16 can be separately molded by various conventional molding techniques such as injection molding, compression molding, blow molding, spin casting, etc. In various embodiments, the head component mold 12 or the stem component mold 16 can also be molded as single pieces.

The halves 20 and 22 and halves 42 and 44, respectively, can be joined substantially along the center line 26 matching the coronal plane by means of a connecting or coupling mechanism 54 on each respective part. In various embodiments, the coupling mechanism 54 can be a tongue and groove coupling mechanism 56 having a substantially rounded tongue 58 running about the outer circumference along the center line or coronal plane 26 of the first half 20 and 42. A rectangular groove 60 can be positioned also substantially around the outer circumference of the second halves 22 and 44 along the coronal plane 26. The tongue 56 can be rounded to provide a self centering mechanism and also to assist in engaging the rounded tongue 56 within the rectangular shaped groove 60 since engaged silicone does not slide readily with respect to one another. In various embodiments, the tongue 58 can be adhered to the groove 60 by use of a silicone adhesive.

The tongue 58 and groove 60 are an exemplary removal mechanism through which separation and tearing of the first half 20 or 42 from the respective second half 22 or 44 is achieved. It should also be noted that any other type of coupling mechanism could also be employed such as two planar surfaces adhered together, differently shaped mating surfaces, etc. Other removal mechanisms can include a pull string or a pull tab as are known in the art. For example, a pull string made of suture, thin metal wire, or the like can be embedded in the thermoplastic mold such that upon pulling or engaging the string, the thermoplastic stretches and tears to expose the implant.

Turning to FIGS. 8 through 12, a modular system having reinforced head molds 112 and reinforced stem molds 116 is provided. The modular systems of such embodiments share similarities with the above-described embodiments and like features are referenced by similar numerals (i.e.: head mold 12 and head mold 112). It is also understood that the components of all embodiments disclosed herein can be interchanged.

The head mold 112 is made of halves 120 and 122 and contains a head connector 114 and a reinforcing core 115. Upon dispensing the cement into the nozzle 136, the reinforcing core 115 is surrounded by the cement. The reinforcing core 115 provides additional support for the cement and increases the strength of the temporary implant. The reinforcing core 115 can be made of a metal or any other suitable material, as is described above. As shown in FIGS. 8 and 10, the core 115 can be formed to include several dimensions and tapered regions or, as shown in FIG. 12, the core 115 can consist of a generally uniformly tapered dimension.

The stem component 116 is made of halves 142 and 144 and includes a stem connector 118 and a reinforcing core 119. The reinforcing core 119 similarly adds further support for the cement and increases the strength of the temporary implant. The reinforcing core 119 can extend the length of the stem component mold 116 as shown in FIG. 10, or the reinforcing core 119 can partly extend along a region of the length of the stem component mold 116. The reinforcing core 119 can be made of a metal or any other suitable material and provides additional support for the cement and increase the strength of the temporary implant.

Figure 9:
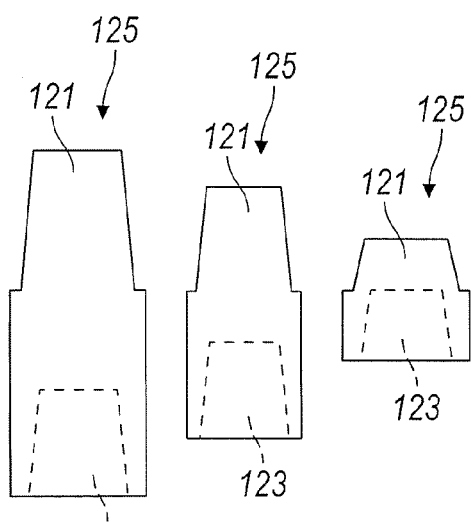
FIG. 9 depicts a series of bridges.

As shown in FIG. 9, a neck adapter or bridge 125 can be connected to either of the head component 112 or the stem component 116. The bridge 125 can be of differing lengths to provide a neck length suitable to the individual needs of the patient. The proximal end 121 of the bridge 125 mates with the head connector 114. The distal end 123 of the bridge 125 mates with the stem connector 118. By varying the length of the bridge 125, the neck length is adapted to provide a highly customized implant to the patient. The use of the bridge 125 is optional as certain patient's may not need the additional neck length.

Figure 7:
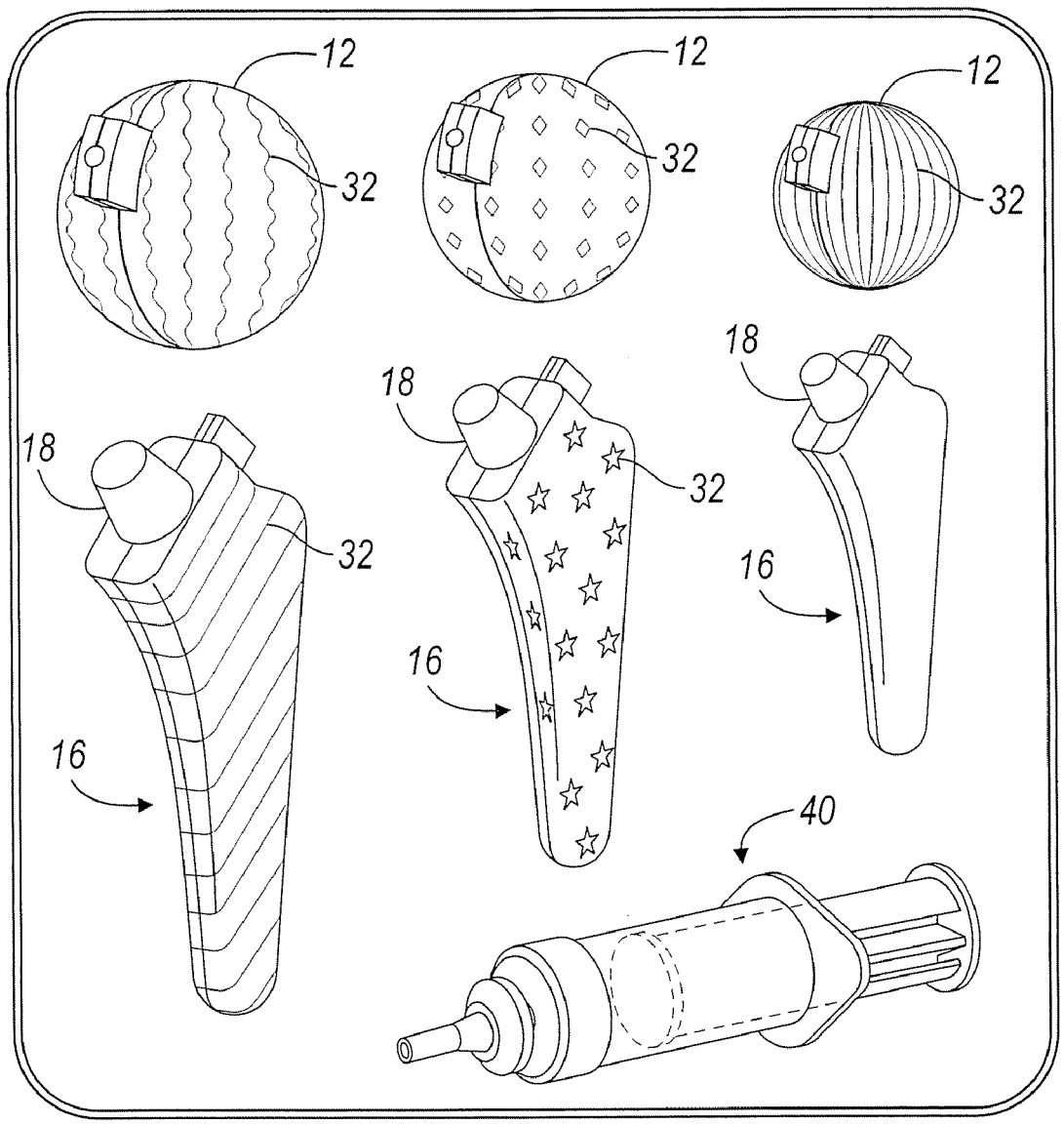
FIG. 7 depicts a kit according to various embodiments.
Figure 8:
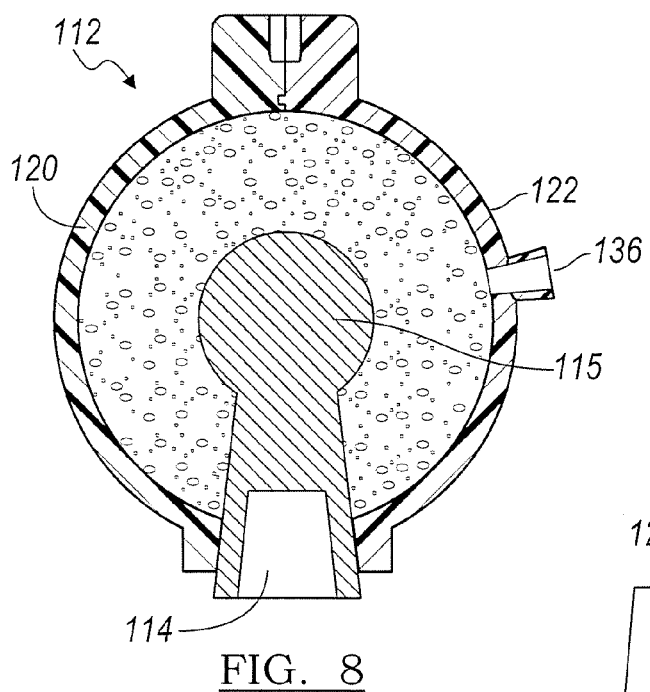
FIG. 8 depicts a head component having a reinforcing head connector therein.

Referring to FIG. 7, a kit 1000 is provided. The kit 1000 can include at least one head component mold 12, at least one stem component mold 16, and at least one stem connector 18. In various embodiments, the kit 1000 can include a plurality of any of the head component mold 12, stem component mold 16, and stem connector 18. The kit 1000 contents can be provided in differing sizes to allow for implant customization. As shown in the kit 1000, a variety of stem connectors 18 are provided being predisposed in the stem component molds 16. Any combination of features and parts as detailed herein can be included in the kit 1000, such as, for example, an inclusion of a variety of differing surface area increasing features 32 being included on the different components or a deliver device(s) 40. The components of the kit 1000 can be individually seated with the outer container. Minor modifications and inclusions in the kit 1000 which are incidental to surgical methods, such as scalpels, antibiotics, cement, gauze, etc. are also included within the scope of the present teachings.

In embodiments using the reinforced molds as detailed above, an exemplary kit 1000 can include at least one of the reinforced head component molds 112, at least one reinforced stem component mold 116, and at least one bridge 125. The contents of the kit 1000 can also include a mixture of components, for example, a plurality of bridges 125 included with at least one reinforced head component molds 112, at least one head component mold 12, and at least one stem component mold 16.

The present teachings further provide methods of using the modular cement mold. Although the methods are disclosed as used with certain embodiments of the present teachings, it is understood that the methods disclosed can be used with any of the mold embodiments detailed above herein.

First, a surgeon or assistant will mix the appropriate antibiotic loaded cement or add an antibiotic to the particular cement. It is understood that the preparation of the cement is performed according to the label instructions of the particular cement. For example, about two grams of antibiotic are mixed with each 40 gram packet of bone cement powder which is then mixed with a corresponding number of 20 milliliter ampoules of a liquid monomer. The bone cement can be a poly-methyl-methacrylate (PMMA) cement such as those produced under the trade names Generation 4(TM), CMW1, CMW2, CMW3, Zimmer Dough Type, or Zimmer LVC, or a MMA-styrene copolymer cement such as that produced under the trade names Howmedia Simplex P or Zimmer Osteobond, or an MMA-methyl acrylate copolymer such as that produced under trade names Cobalt (TM) G-HV or Cobalt (TM) HV. Once the appropriate antibiotic loaded bone cement is mixed, the bone cement is put within the delivery device 40 shown as a cement gun.

As shown in FIG. 6, with the delivery device 40 loaded with the bone cement, the appropriately sized modular components 12 and 14 are selected to form a customized fit for both the articulating head and femoral component of the final implant. For example, the appropriately sized modular components 12 and 14 along with the stem connector 18 can be selected from the kit 1000 as shown in FIG. 7 to meet the patient's needs. Once the appropriately sized modular components 12, 14, and 18 are selected, a surgeon will generally grasp the head component mold 12 and slidably and sealably insert the nozzle 38 of the delivery device 40 into the access port 36. With the nozzle 38 substantially sealing the access port 36, the surgeon will engage the delivery device 40 to dispense out the bone cement within the inner spherical walls 30 of the head component mold 12.

As the bone cement is delivered within the head component mold 12, air trapped within the head component mold 12 can be released using optional vent holes 62. The vent holes 62 can be located along the center line 26, opposite the access port 36, or at an offset of 15° to 30° from the center line 26, as non-limiting examples. The vent holes 62 are positioned so that any trapped air can be evacuated from the system. The vent holes 62 are sized to allow passage of air but to restrict or block passage of bone cement out of the mold. In various embodiments, the access port 36 can be somewhat flexible to allow the surgeon to angle or direct the nozzle 38 within the head component mold 12 to insure that the head component mold 12 is fully filled with the bone cement.

Using a translucent or transparent material to form the mold allows the surgeon to assess whether the head component mold 12 has been adequately filled without substantially any air pockets or voids. This also allows the surgeon to verify that the surface features 32 have been adequately navigated by the cement to provide the proper surface area.

Turning to FIG. 5, with respect to the stem component mold 16, the stem connector 18 can be selected to provide the appropriate neck extension on the stem portion of the implant. The surgeon then places the stem connector 18 into the stem component mold 16 by angling the stem connector 18 in the opening 17 defined by the stem component mold 16. As shown in FIG. 1, the stem connector 18 can be backed into the stem component mold 16. The surgeon then manipulates the stem connector 18 such that the system becomes material-tight or is a closed system except for inlet of the cement into the access port 36. Similar to the technique to fill the head component mold 12, the surgeon inserts the delivery device 40 into the access port 36 and fills the stem component mold 16 with the cement. In embodiments where the access port 36 is placed at point along the stem component mold 16 which is distal to the stem connector 18, deposition of the cement further presses the stem connector 18 against the opening 17 in the stem component mold 16.

Once the modules of the cement mold 10 are filled by the delivery device 40, the modules 12 and 14 can be placed on a nearby surface, such as a surgical table, to allow the cement to cure and cool while the surgeon moves on to another task, thereby substantially increasing the efficiency and reducing the time for the surgical procedure. In various embodiments, the modules 12 and 14 can be placed on the surgical table such that the foot 34 engages the table. Once the bone cement has sufficiently cured, the surgeon can grasp the modules via the foot 34 and then slips his thumbs within a cut-out region 64 to disengage the tongue and groove coupling. In embodiments using silicone, the tear characteristics of the silicone material allow the modules to be torn from the formed cement. The combined cement and the respective head connector 14 and stem connector 18 form composite implants of the combined materials.

The stem component of the temporary hip implant can then be simply engaged in the intramedullary canal of the host femur. The stem connector 18 is then disposed in the head connector 14 of the articulating head using the taper fit. This allows for quick and easy placement and enables the distended joint to be subsequently re-engaged with the temporary implant to enable limited non-load bearing movement by the patient. The temporary implant allows the patient to generally sit up or be transported out of a hospital during the temporary recovery stage prior to having a revision type prosthesis subsequently implanted. During this time the antibiotic in the bone cement leaches out over time to the infected area and soft-tissue tension is maintained.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A modular articulating cement spacer mold for forming a temporary implant comprising:
   a head component mold defining a first opening therein;
   a head connector positioned within the first opening of the head component mold;
   a stem component mold defining a second opening therein; and
   a stem connector to fit within the second opening of the stem component mold and mateably engage the head connector.

2. The modular articulating cement spacer mold according to claim 1, wherein at least one of the head component mold and the stem component mold includes at least one surface area increasing feature thereon.

3. The modular articulating cement spacer mold according to claim 1, wherein at least one of the head component mold and the stem component mold include a plurality of surface area increasing features thereon.

4. The modular articulating cement spacer mold according to claim 2, wherein the surface area increasing feature is selected from the group consisting of grooves, notches, dimples, stars, hemispheres, cones, ridges, and combinations thereof.

5. The modular articulating cement spacer mold according to claim 1, wherein at least one of the head component mold and the stem component mold further defines an input port being operably sealable to receive a delivery nozzle.

6. The modular articulating cement spacer mold according to claim 1, wherein the head component mold and the stem component mold are made of a silicone polymer.

7. The modular articulating cement spacer mold according to claim 1, wherein at least one of the head component mold and the stem component mold include a removal mechanism operable to assist in removal of the mold from a cement.

8. The modular articulating cement spacer mold according to claim 7, wherein the removal mechanism is selected from the group consisting of a tongue and groove connection, a pull string, a pull tab, and combinations thereof.

9. The modular articulating cement spacer mold according to claim 1, wherein the head connector and the stem connector are made of a biocompatible metal and mateably fit together with a taper fit.

10. The modular articulating cement spacer mold according to claim 1, wherein the stem connector is moveable with respect to the stem component mold.

11. The modular articulating cement spacer mold according to claim 10, wherein movement of the stem component mold upon filling the stem component mold with a filling material maintains the sealed integrity of the stem component mold.

12. The modular articulating cement spacer mold according to claim 1:
   wherein the head component mold and the stem component mold include a plurality of surface area increasing features thereon, wherein the surface area increasing features are independently selected from the group consisting of grooves, notches, dimples, stars, hemispheres, cones, ridges, and combinations thereof;
   wherein the head component mold and the stem component mold each define an input port being operably sealed to receive a delivery nozzle; and
   wherein the head component mold and the stem component mold include a removal mechanism selected from the group consisting of a tongue and groove connection, a pull string, a pull tab, and combinations thereof operable to assist in the removal of the mold from a cement.

13. A kit for forming modular articulating cement spacer mold for forming temporary implants comprising:
   at least one head component mold defining a first opening therein;
   at least one head connector positioned within the first opening of the head component mold
   at least one stem component mold defining a second opening therein; and
   at least one stem connector to fit within the second opening of the stem component mold and mateably engage the head connector.

14. The kit according to claim 13 further comprising a plurality of head component molds of different sizes.

15. The kit according to claim 13 further comprising a plurality of stem component molds of different sizes.

16. The kit according to claim 13 further comprising a plurality of bridge adapters of different sizes.

17. The kit according to claim 13, wherein at least one of the head component mold and the stem component mold have surface features thereon to provide an imprint on the temporary implant.

18. The kit according to claim 17, wherein the surface area increasing features are selected from the group consisting of grooves, notches, dimples, stars, hemispheres, cones, ridges, and combinations thereof.

19. The kit according to claim 13 further comprising a dispensing device.

20. The kit according to claim 13 further comprising at least one of a bone cement or an antibiotic.

21. The kit according to claim 13 comprising:
   a plurality of head component molds of different sizes wherein at least one head component mold has at least one surface area increasing feature thereon;
   a plurality of stem component molds of different sizes wherein at least one stem component mold has at least one surface area increasing feature thereon;
   a plurality of bridge adapters of different sizes;
   a cement;
   an antibiotic; and
   a dispensing device.

22. A modular articulating cement spacer mold for forming a temporary implant comprising:
   a head component mold defining a first opening therein;
   a head connector positioned within the first opening of the head component mold, wherein the head connector is movable with respect to the head connector mold;
   a stem component mold defining a second opening therein; and
   a stem connector configured to fit within the second opening of the stem component mold and to link with the head connector, wherein the stem connector is movable with respect to the stem component mold;
   wherein the head component mold and the stem component mold include a plurality of surface area increasing features thereon, wherein the surface area increasing features are independently selected from the group consisting of grooves, notches, dimples, stars, hemispheres, cones, ridges, and combinations thereof;
   wherein the head component mold and the stem component mold each define an input port being operably sealed to receive a delivery nozzle; and
   wherein the head component mold and the stem component mold include a removal mechanism selected from the group consisting of a tongue and groove connection, a pull string, a pull tab, and combinations thereof.

23. The modular articulating cement spacer mold according to claim 22, wherein movement of the stem component mold upon filling the stem component mold with a filling material maintains sealed integrity of the stem component mold.

24. The modular articulating cement spacer mold according to claim 22, wherein the head component mold and the stem component mold are made of a silicone polymer.

25. The modular articulating cement spacer mold according to claim 22, wherein the removal mechanism is operable to assist in the removal of the mold from a cement.

* * * * *